United States Patent
Chow et al.

(10) Patent No.: US 6,692,466 B1
(45) Date of Patent: Feb. 17, 2004

(54) DRUG DELIVERY CATHETER WITH RETRACTABLE NEEDLE

(75) Inventors: Mina Chow, Campbell, CA (US); Paul John Kawula, Sunnyvale, CA (US); Jeffrey Steward, Lakewood, CO (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 17 days.

(21) Appl. No.: 09/746,498

(22) Filed: Dec. 21, 2000

(51) Int. Cl.[7] ............................................. A61M 5/178
(52) U.S. Cl. ........................... 604/164.01; 604/164.03; 604/164.13; 604/96.01; 604/264
(58) Field of Search ....................... 604/164.01–164.04, 604/164.13, 264, 96.01, 99.01, 158, 239

(56) References Cited

U.S. PATENT DOCUMENTS

| | | |
|---|---|---|
| 3,598,119 A | 8/1971 | White |
| 4,771,777 A * | 9/1988 | Horzewski et al. ......... 606/194 |
| 5,354,279 A | 10/1994 | Höfling |
| 5,464,395 A * | 11/1995 | Faxon et al. ........... 604/103.02 |
| 5,693,029 A | 12/1997 | Leonhardt |
| 5,746,716 A | 5/1998 | Vigil et al. |
| 6,051,008 A | 4/2000 | Saadat et al. |
| 6,102,887 A * | 8/2000 | Altman ..................... 604/264 |
| 6,102,926 A | 8/2000 | Tartaglia et al. |
| 6,120,520 A | 9/2000 | Saadat et al. |
| 6,217,554 B1 | 4/2001 | Green |
| 6,270,477 B1 * | 8/2001 | Bagaoisan et al. ...... 604/102.01 |
| 6,283,947 B1 * | 9/2001 | Mirzaee ..................... 604/264 |

* cited by examiner

Primary Examiner—Gregory L. Huson
Assistant Examiner—Amanda Flynn
(74) Attorney, Agent, or Firm—Blakely, Sokoloff, Taylor & Zafman LLP

(57) ABSTRACT

A catheter assembly having a balloon disposed at the distal end thereof and a therapeutic substance delivery assembly, including a needle in fluid communication with a therapeutic substance delivery lumen for allowing a therapeutic substance to be injected into a diseased physiological lumen. A deflector is positioned along an inside wall of the delivery lumen, positioned, such that as a bend region forms caused by the movement of the delivery lumen, the deflector bends to rest on the outside curvature of the bend. As the needle is made to travel through the bend, the ribbon helps to bounce the needle tip off the wall of the delivery lumen, allowing the needle to travel through the bend without digging into and/or gouging the delivery lumen wall.

25 Claims, 7 Drawing Sheets

DRUG DELIVERY CATHETER WITH RETRACTABLE NEEDLE

BACKGROUND OF THE INVENTION

1. Field of the Invention

The present invention relates to a medical device for delivering a substance to a vascular lumen. More specifically, the present invention relates to a catheter for delivering a therapeutic substance to a location within a physiological lumen and adjacent tissue/vascular structure.

2. Relevant Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress the atherosclerotic plaque of the lesion against the inner wall of the artery to dilate the lumen. The balloon is then deflated to a smaller profile to allow the catheter to be withdrawn from the patient's vasculature.

Restenosis of the artery commonly develops over several months after the procedure, which may require another angioplasty procedure or a surgical by-pass operation. Restenosis is thought to involve the body's natural healing process. Angioplasty or other vascular procedures injure the vessel walls, removing the vascular endothelium, disturbing the tunica intima, and causing the death of medial smooth muscle cells. Excessive neoinitimal tissue formation, characterized by smooth muscle cell migration and proliferation to the intima, follows the injury. Proliferation and migration of smooth muscle cells (SMC) from the media layer to the intima cause an excessive production of extra cellular matrices (ECM), which is believed to be one of the leading contributors to the development of restenosis. The extensive thickening of the tissues narrows the lumen of the blood vessel, constricting or blocking blood flow through the vessel.

To reduce the chance of the development of restenosis, therapeutic substances are administered to the treatment site. For example, anticoagulant and antiplatelet agents are commonly used to inhibit the development of restenosis. In order to provide an efficacious concentration to the target site, systemic administration of such medication often produces adverse or toxic side effects for the patient. Local delivery is a preferred method of treatment in that smaller total levels of medication are administered in comparison to systemic dosages, but are concentrated at a specific site. Local delivery, thus, produces fewer side effects and achieves more effective results.

One commonly applied technique for the local delivery of a therapeutic substance is through the use of a medicated, implantable prosthesis, one example of which includes a stent. A stent coated with a polymeric carrier, which is impregnated with a therapeutic substance, can be deployed at a selected site of treatment. The polymeric carrier allows for a sustained delivery of the therapeutic substance. A disadvantage associated with the use of medicated stents is that the quantity of the substance that can be impregnated in the polymeric carrier is limited. In order to increase the capacity of the polymeric carrier, the amount of polymeric material employed, and in effect the thickness of the coating must be increased to accommodate the quantity of the substance used. An increase in the profile of the coating significantly limits the applications for which the stents can be used.

One technique for the local delivery of a therapeutic substance into the tissue surrounding a bodily passageway is disclosed in U.S. Pat. No. 5,464,395, to Faxon et al. Faxon et al. discloses a catheter including a needle canula slidably disposed in a needle lumen and a balloon, which is coupled to the distal end of the catheter. When the balloon is inflated the needle lumen is brought into close engagement with the tissue and the needle canula can be moved between a position inboard of the catheter distal surface and a position where the needle canula is projected outboard of the catheter to deliver the therapeutic substance to the tissue.

It has been observed, that in most instances the inflation and deflation of the balloon causes the needle lumen to form a tortuous pathway, which the needle canula must traverse to reach the tissue. Unfortunately, under these conditions the needle canula can become stuck in the pathway, such that it cannot be advanced. For example, the sharp tip of the needle canula can gouge, become lodged in, or puncture the catheter wall. Curving the tip of the needle may help to prevent some damage, but it can require that the needle lumen be made undesirably larger to accommodate the curved needle tip and may result in inconsistent needle engagement with the tissue.

SUMMARY

The present invention provides a substance delivery apparatus which can be used to provide local drug therapies to a diseased physiological lumen, for example, to prevent or treat arterial restenosis and to promote angiogenesis response in the ischemic heart. A catheter assembly is provided having a balloon disposed at the distal end thereof. The balloon is capable of being inflated to selectively dilate from a collapsed configuration to an expanded configuration. The balloon is also capable of being deflated after inflation to return to the collapsed configuration or a deflated profile. A therapeutic substance delivery assembly, which can include a needle disposed in delivery lumen, is provided on the catheter assembly for allowing a therapeutic substance to be delivered through the needle and injected into a tissue of the physiological lumen. The delivery lumen defines two sections created as a bend region forms between the sections, as one section moves/rotates relative to the other section. The movement of one section relative to the other section is generally from a first position towards a second position in response to the balloon being inflated from the collapsed configuration to the expanded configuration. The delivery lumen is capable of moving from the second position back towards the first position when the balloon is being deflated.

In accordance with the present invention, a deflector, such as a thin metallic ribbon member, can be positioned along an inside wall of the delivery lumen. The deflector can be positioned, such that as the bend region forms caused by the movement of the sections, the deflector bends to rest on the outside curvature of the bend region. The needle is inserted into the delivery lumen and is urged distally to travel through the bend from a first position, where the needle is retracted within the delivery lumen, to a second position, where the needle extends a distance out from an opening in the delivery lumen.

As the needle travels through the bend region, the ribbon member allows the needle tip to bounce or be deflected off the wall of the delivery lumen, allowing the needle to travel through the bend without puncturing, gouging, or otherwise damaging the wall of the delivery lumen. Since the ribbon member can be made relatively small, the catheter track performance is not compromised. Advantageously, using the ribbon member avoids the need to modify the tip of the needle, thus maintaining a low catheter profile and a consistent needle engagement with the physiological lumen tissue.

These and other features and advantages of the present invention will be more readily apparent from the detailed description of the embodiments, set forth below, taken in conjunction with the accompanying drawings.

BRIEF DESCRIPTION OF THE DRAWINGS

The features of the described embodiments are specifically set forth in the appended claims. However, the embodiments are best understood by referring to the following description and accompanying drawings, in which similar parts are identified by like reference numerals.

DETAILED DESCRIPTION

Figure 1A:
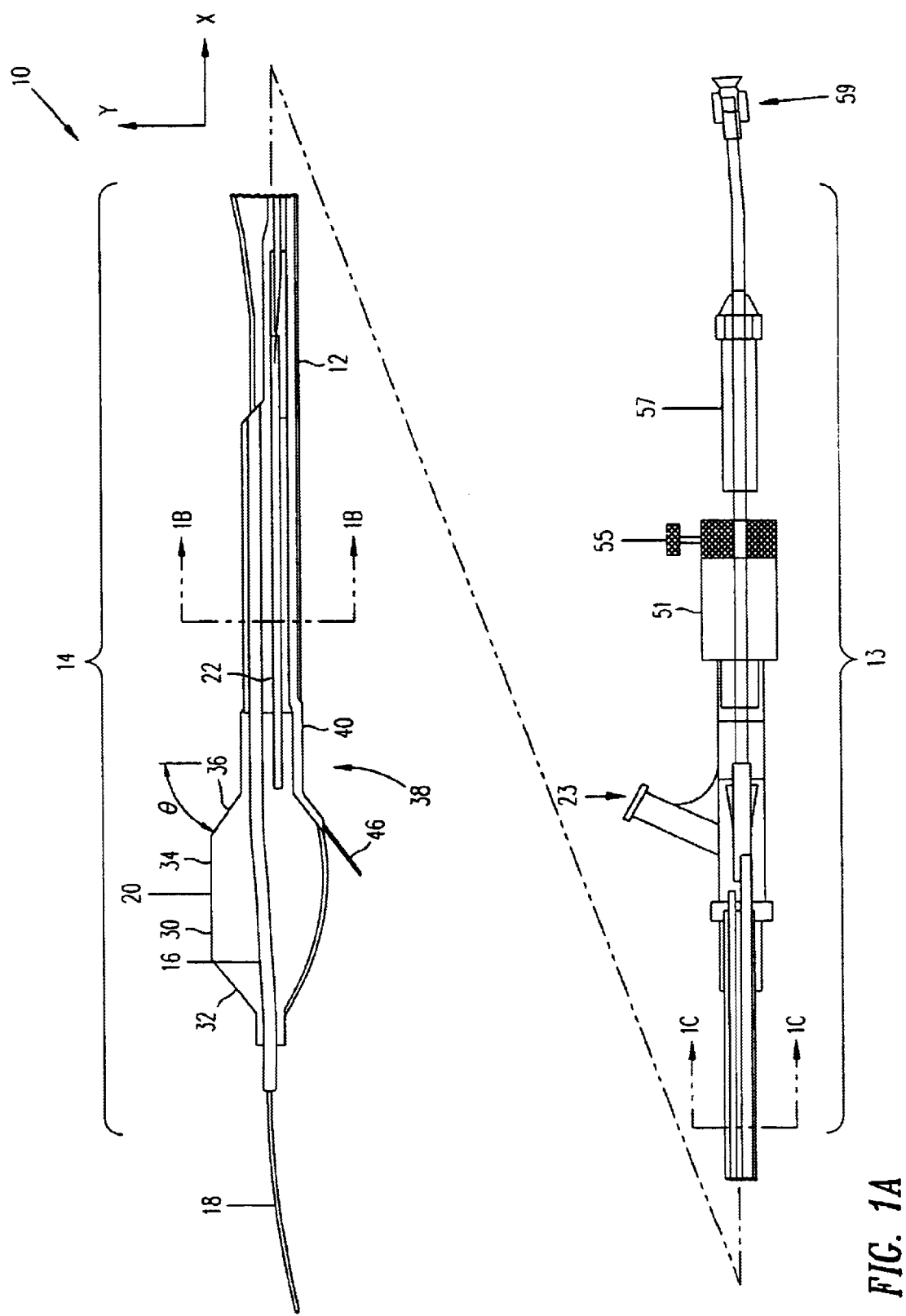
FIG. 1A is a simplified sectional view of an embodiment of a substance delivery apparatus in the form of a catheter assembly having a balloon and a therapeutic substance delivery assembly.
Figure 1B:
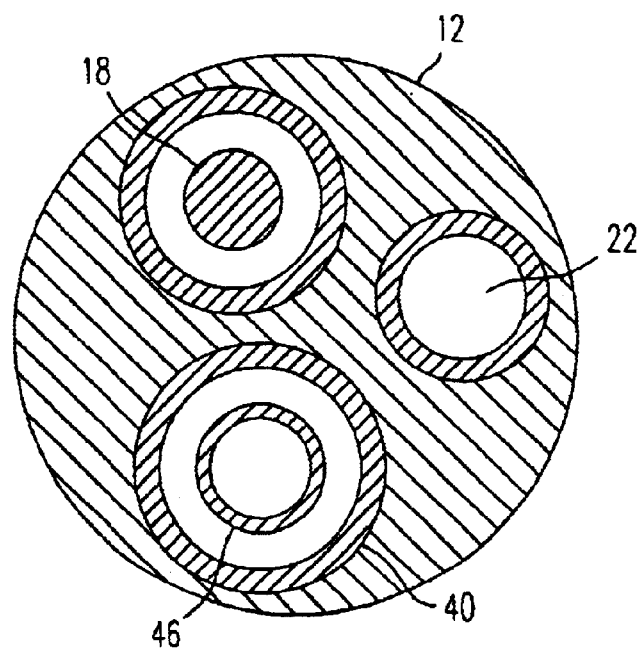
FIGS. 1B and 1C are cross-sectional views of the distal and proximal ends, respectively, of the apparatus of FIG. 1A.
Figure 1C:
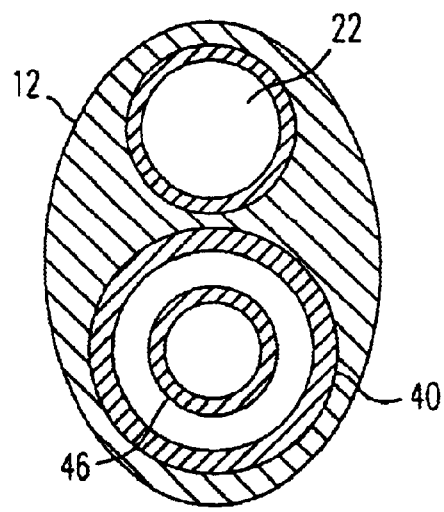

Referring now to the drawings, wherein similar parts are identified by like reference numerals, FIGS. 1A, 1B, and 1C illustrate a substance delivery apparatus in accordance with one embodiment of the invention. In general, the substance delivery apparatus provides a system for delivering a substance, such as a therapeutic substance or a combination of therapeutic substances, to or through a desired area of a physiological lumen in order to treat a localized area of the lumen or to treat a localized area of tissue located adjacent to the lumen. The substance delivery apparatus includes a catheter assembly 10, which is intended to broadly include any medical device design for insertion into a physiological lumen to permit injection and/or withdrawal of fluids, to maintain the patency of the lumen, or for any other purpose. It is contemplated that the substance delivery apparatus has applicability for use with any physiological lumen, including blood vessels, urinary tract, intestinal tract, kidney ducts, wind pipes, and the like.

In one embodiment, catheter assembly 10 is defined by an elongated catheter body 12 having a proximal end 13 and a distal end 14. Catheter assembly 10 can include a guidewire lumen 16 for allowing catheter assembly 10 to be fed and maneuvered over a guidewire 18. A balloon 20 is incorporated at distal end 14 of catheter assembly 10 and is in fluid communication with an inflation lumen 22 of catheter assembly 10.

Balloon 20 can be formed from a balloon wall or membrane 30 which is selectively inflatable to dilate from a collapsed configuration to a desired and controlled expanded configuration. Balloon 20 can be selectively inflated by supplying a fluid into inflation lumen 22 at a predetermined rate of pressure through an inflation port 23. Balloon wall 30 is selectively deflatable, after inflation, to return to the collapsed configuration or a deflated profile. In one embodiment, balloon wall 30 can be defined by three sections, a distal taper wall 32, a medial working length 34, and a proximal taper wall 36. In one embodiment, proximal taper wall 36 can taper at any suitable angle θ, typically between about 15° to less than about 90°, when balloon 20 is in the expanded configuration.

The three sections 32, 34, and 36 can be bound together by seams or be made out of a single seamless material. Balloon 20 can be made from any suitable material, including, but not limited to, polymers and copolymers of polyolefins, polyamides, polyesters and the like. The specific material employed must be mutually compatible with the fluids employed in conjunction with balloon 20 and must be able to stand the pressures that are developed within balloon 20. Balloon wall 30 can have any suitable thickness so long as the thickness does not compromise properties that are critical for achieving optimum performance. The properties include high burst strength, low compliance, good flexibility, high resistance to fatigue, the ability to fold, the ability to cross and recross a desired region of treatment or an occluded region in a lumen, and low susceptibility to defect caused by handling. By way of example, and not limitation, the thickness can be in the range of about 10 microns to about 30 microns, the diameter of balloon 20 in the expanded configuration can be in the range of about 2 mm to about 10 mm, and the length can be in the range of about 3 mm to about 40 mm, the specific specifications depending on the procedure for which balloon 20 is to be used and the anatomy and size of the target lumen in which balloon 20 is to be inserted.

Balloon 20 may be inflated by the introduction of a liquid into inflation lumen 22. Liquids containing therapeutic and/or diagnostic agents may also be used to inflate balloon 20. In one embodiment, balloon 20 may be made of a material that is permeable to such therapeutic and/or diagnostic liquids. To inflate balloon 20, the fluid can be supplied into inflation lumen 22 at a predetermined pressure, for example, between about 1 and 20 atmospheres. The specific pressure depends on various factors, such as the thickness of balloon wall 30, the material from which balloon wall 30 is made, the type of substance employed, and the flow-rate that is desired.

Catheter assembly 10 also includes a therapeutic substance delivery assembly 38 for injecting a therapeutic substance into a tissue of a physiological passageway. In one embodiment, delivery assembly 38 includes a needle 46 movably disposed within a hollow delivery lumen 40. Delivery lumen 40 extends between distal end 14 and proximal end 13. Delivery lumen 40 can be made from any suitable material, such as polymers and copolymers of polyamides, polyolefins, polyurethanes, and alike. Access to the proximal end of delivery lumen 40 for insertion of needle 46 is provided through a hub 51.

Figure 2A:
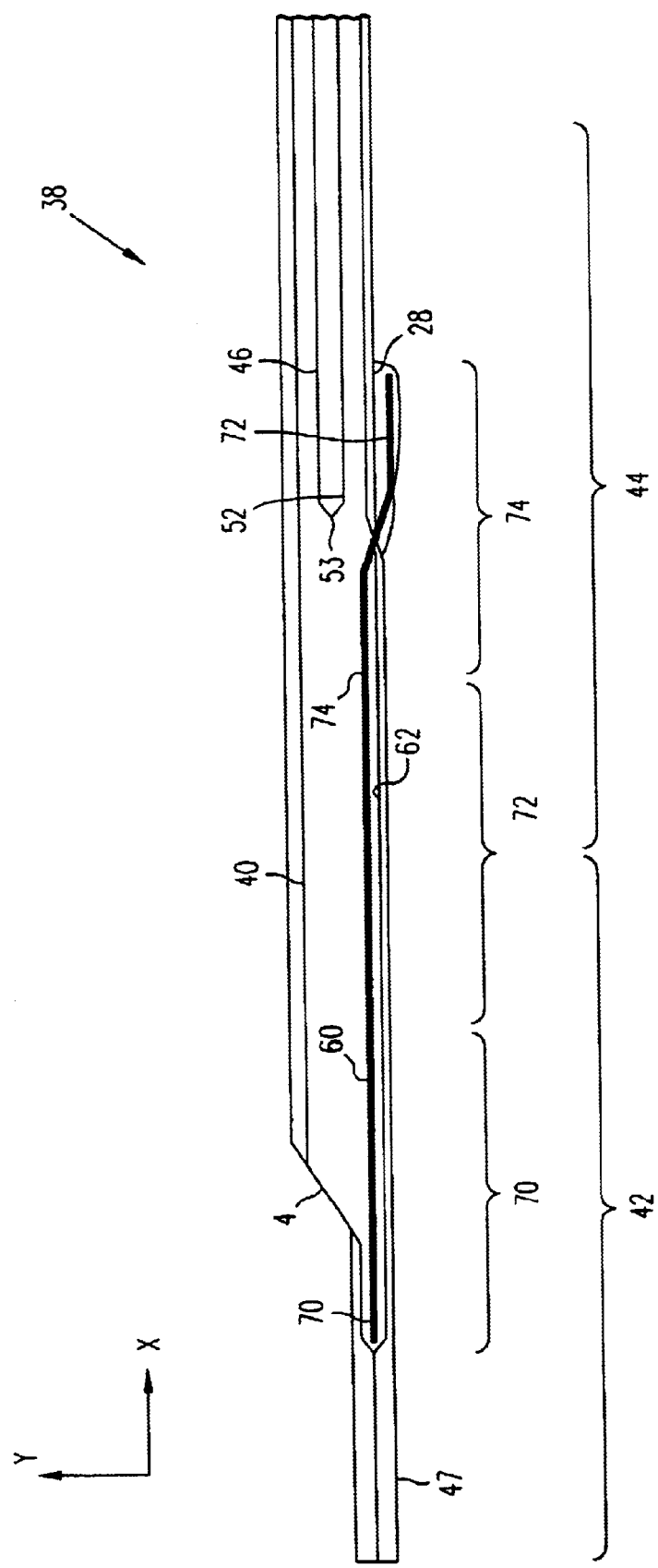
FIGS. 2A and 2B are simplified sectional views of the deflector of the present invention.
Figure 2B:
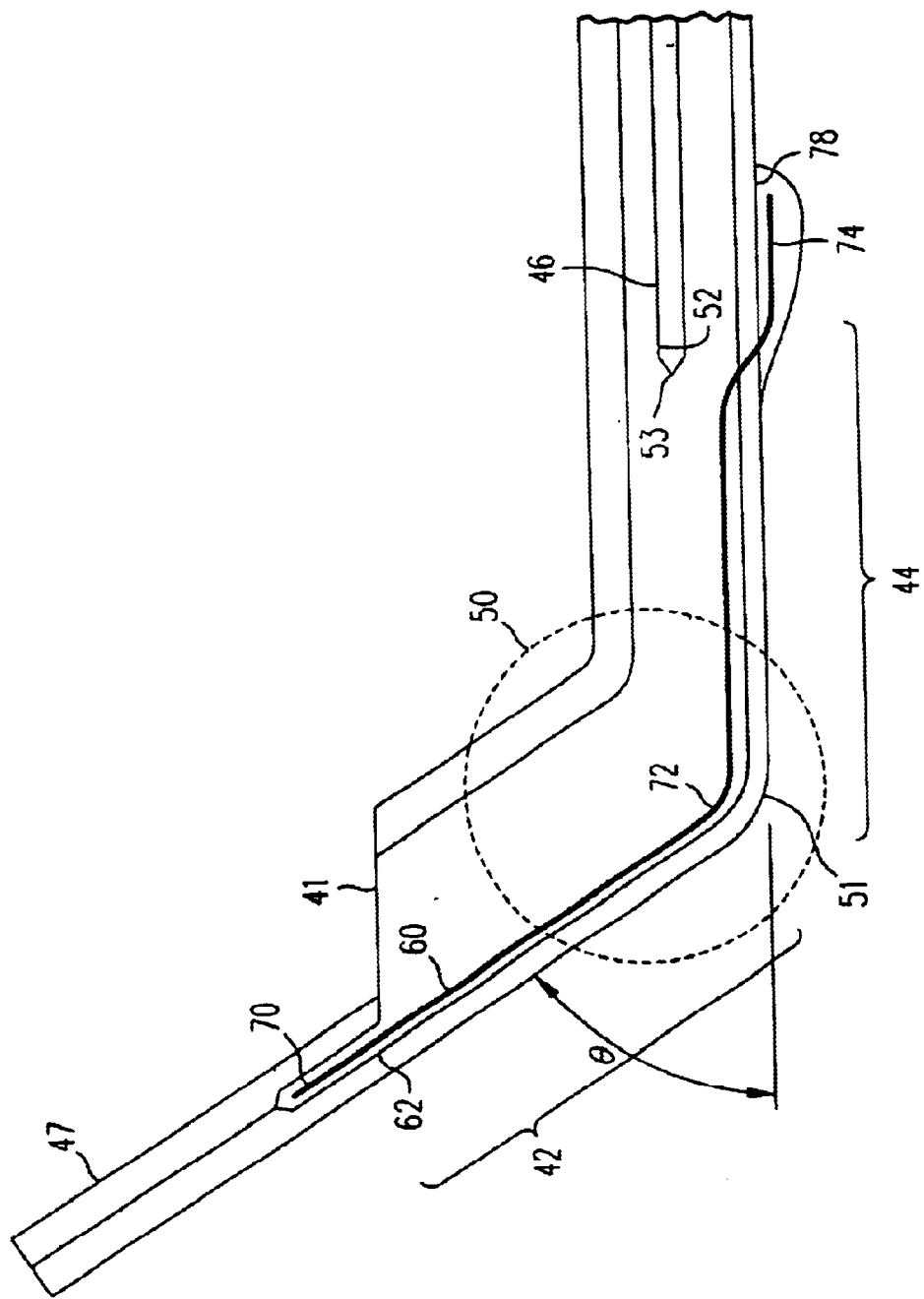
Figure 3A:
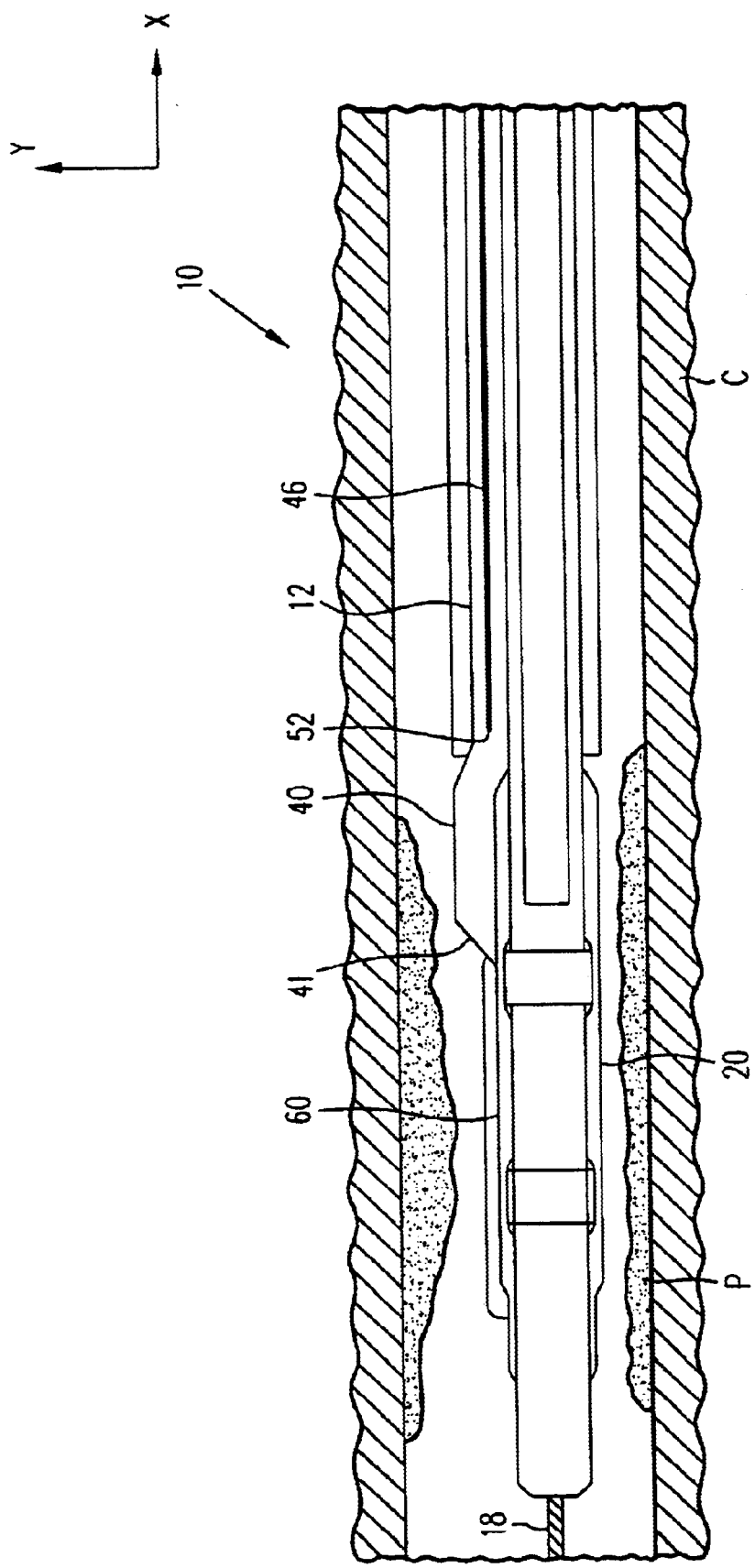
FIG. 3A is a simplified partial sectional view of an embodiment of the substance delivery apparatus in the form of a catheter assembly having a balloon in a deflated configuration and the therapeutic substance delivery assembly.
Figure 3B:
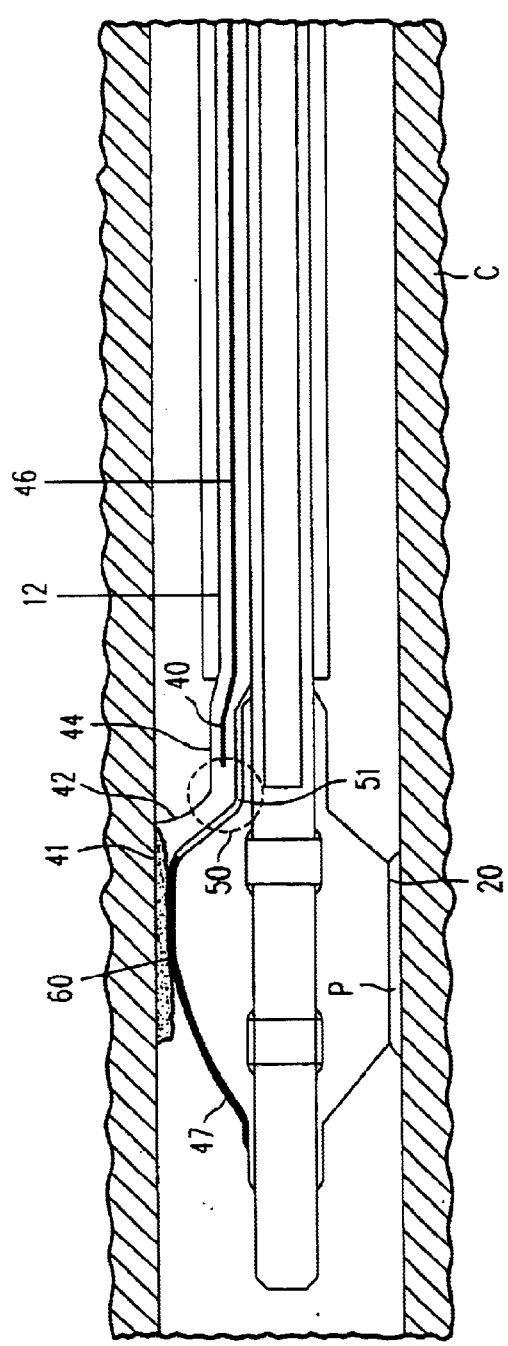
FIG. 3B is a simplified partial sectional view of an embodiment of the substance delivery apparatus in the form of a catheter assembly having a balloon in an expanded configuration and the therapeutic substance delivery assembly having the needle in a retracted position.

FIGS. 2A and 2B are simplified sectional views of therapeutic substance delivery assembly 38 in an undeployed and deployed arrangement, respectively. Delivery lumen 40 defines a distal or first section 42 and a proximal or second section 44. Distal section 42 can include an overhang section 47 that extends beyond opening 41 to provide a means for securing delivery lumen 40 to balloon 20. For example, overhang section 47 can be adhered along the proximal taper and working length of balloon 20 (FIG. 3B). In this manner, delivery lumen 40 is continually supported during, until, and after needle 46 is extended from delivery lumen 40. In one embodiment, as shown in FIG. 2B, delivery lumen 40 includes a bend region 50 at which distal section 42 of delivery lumen 40 is capable of bending (or generally rotating) about a pivotal point 51 with respect to proximal section 44. For example, to accomplish the pivotal movement, distal section 42 of delivery lumen 40 is in contact with proximal taper wall 36 of balloon 20 (FIG. 1A). Accordingly, in response to the inflation of balloon 20, section 42 moves relative to section 44 to form bend region 50. In one embodiment, section 42 can move from a substantially longitudinal position to a substantially perpendicular position. Thus, the angle θ of the bend region can vary between 0° and 90°. In one example, after inflation of balloon 20, angle θ can range from between about 30° and 60°, for example, 45°.

Needle 46 is slidably or movably disposed in delivery lumen 40. Needle 46 includes a tissue-piercing tip 52 having a dispensing port 53. Dispensing port 53 is in fluid communication with a central lumen (not shown) of needle 46. In one embodiment, the central lumen of needle 46 can be pre-filled with a measured amount of a therapeutic substance. The central lumen of needle 46 connects dispensing port 53 with therapeutic substance injection port 59, which is configured to be coupled to various substance dispensing means of the sort well known in the art, for example, a syringe or fluid pump. Injection port 59 allows the measured therapeutic substance to be dispensed from dispensing port 53 as desired or on command.

Needle 46 is coupled at proximal end 13 of catheter assembly 10 in a needle lock 55. Needle lock 55 can be used to secure needle 46 in position once needle 46 has been either retracted and/or extended from delivery lumen 40 as described below. In one embodiment, an adjustment knob 57 can be used to set the puncture distance of needle 46 as it is extended out from delivery lumen 40 and into the wall of the physiological lumen. For example, adjustment knob 57 may have calibrations, such that each revolution of the adjustment knob from one calibrated mark to another represents a fixed distance of travel for needle 46. The portion of needle 46 protruding from delivery lumen 40 can be of any predetermined length, the specific length being dependent upon the desired depth of calibrated penetration and the procedure for which delivery assembly 38 is to be used. The protruding length of needle 46 can be from about 250 microns to about 4 cm.

Figure 4A:
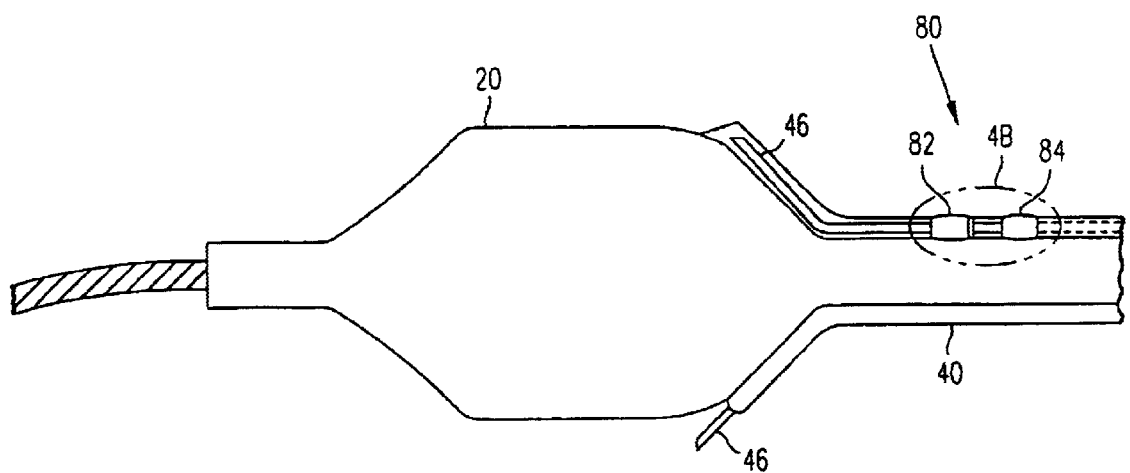
FIG. 4A is a simplified illustration of an embodiment of a mechanical stop for the substance delivery assembly.
Figure 4B:
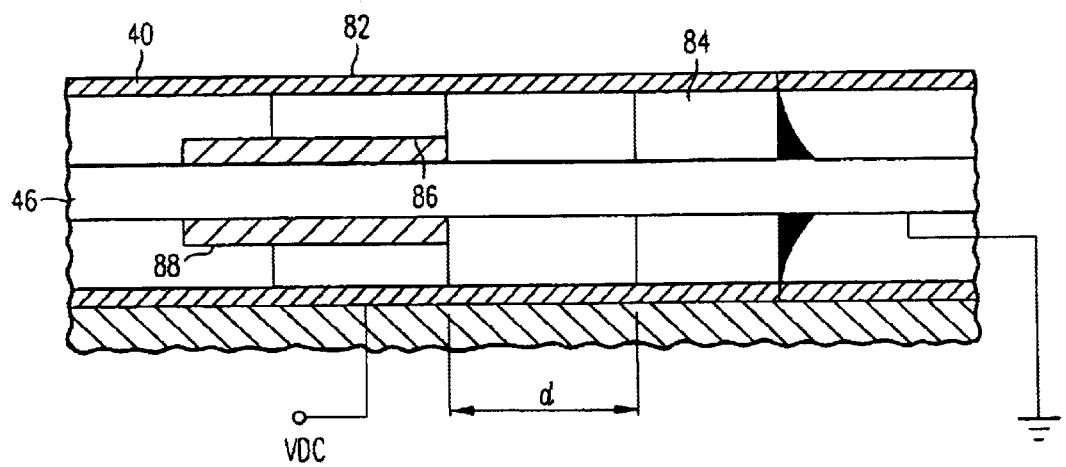
FIG. 4B is a simplified illustration of a portion of the mechanical stop of FIG. 4A.

In the alternative embodiment, shown in FIGS. 4A and 4B, a mechanical stop 80 can be used to limit the travel of needle 46 within delivery lumen 40, which provides control over the depth of penetration. In this alternative embodiment, mechanical stop 80 includes a ring stop 82 and a contact stop 84. Ring stop 82 can be a conductive material, such as a copper metal ring, placed around a circumference of needle 46 within delivery lumen 40. Ring stop 82 is attached to delivery lumen 40 using conventional means, such that ring stop 82 is held stationary as needle 46 slides through an internal diameter 86 of ring stop 82. A low friction, electrically insulating material 88, such as TEFLON® or others well know to those of ordinary skill in the art, can be placed between needle 46 and internal diameter 86 of ring stop 82. Contact stop 84 can be coupled to needle 46 by soldering, welding, gluing and the like, such that contact stop 84 moves with needle 46. Contact stop 84 can be positioned a distance d from ring stop 82. Distance d represents the depth of penetration desired for needle 46. As needle 46 is urged through delivery lumen 40, contact stop 84 approaches ring stop 82. Upon contact, forward movement of needle 46 is impeded. Optionally, contact stop 84 can be grounded while ring stop 82 can be coupled to a voltage source, for example a 5 volt DC battery. In this optional embodiment, contact between ring stop 82 and contact stop 84 completes an electrical circuit, which may include an alarm, such as a beep or a flashing LED, to indicate to the user that the limit has been reached.

In one embodiment, needle 46 is removable from delivery lumen 40 which allows for exchange of needle 46. For example, needle 46 can be exchanged if needle 46 is damaged during a procedure, if a different-sized needle 46 is desired for use in a specific application, and/or if a new therapeutic substance is required.

Figure 3C:
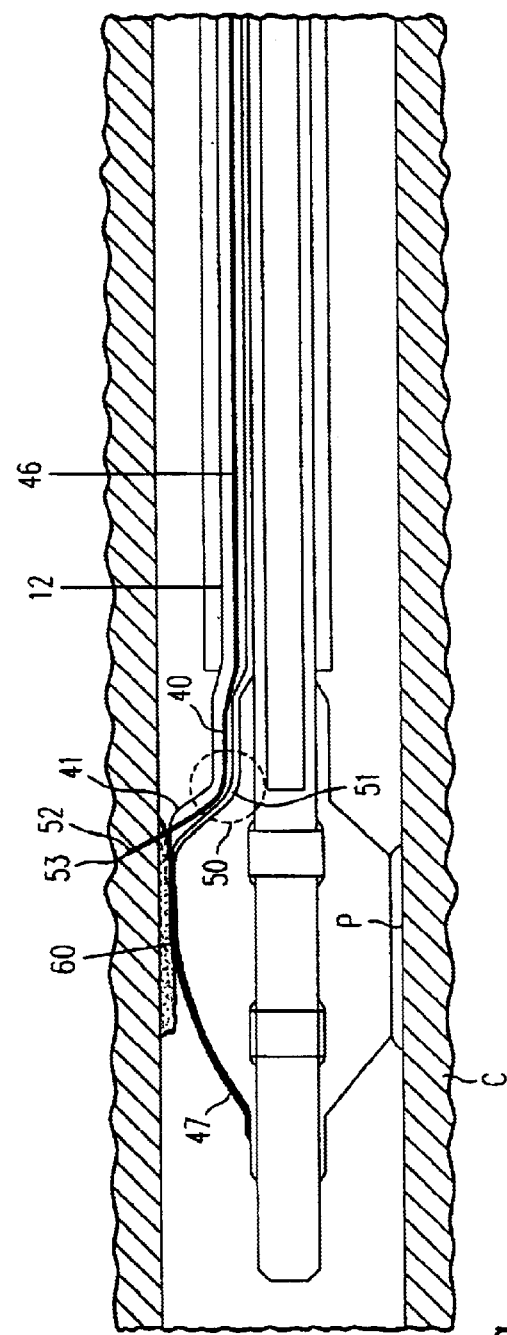
FIG. 3C is a simplified partial sectional view of an embodiment of the substance delivery apparatus in the form of a catheter assembly having a balloon in an expanded configuration and the therapeutic substance delivery assembly having the needle in an extended position.

Needle 46 is slidably disposed in delivery lumen 40, so that it can move between a first retracted position (FIG. 3B) and a second extended position (FIG. 3C). In its first or retracted position, tissue-piercing tip 52 is located inboard of the distal surface of catheter body 12, so as to avoid damaging tissue during deployment of catheter assembly 10. In its second or extended position, tissue-piercing tip 52 is located outboard of the distal surface of catheter body 12, so as to permit needle tip 52 to penetrate the tissue surrounding the physiological passageway in which catheter assembly 10 is disposed.

In one embodiment, the delivery apparatus can include any suitable number of delivery assemblies 38, disposed about the periphery of balloon 20 and in communication with proximal taper wall 36. Each of delivery assemblies 38 can include delivery lumens 40 having slidably disposed needles 46 which are in fluid communication with a common source supply of a therapeutic substance. Each of delivery assemblies 38 is, therefore, capable of injecting the same therapeutic substance or the same combination of therapeutic substances. Alternatively, substance delivery lumens 40 can be independent lumens, which can independently supply each needle 46 from a different source of the therapeutic substance or with different combinations of substances. Beneficially, in the alternative example, if an interruption of the flow of therapeutic substance occurs through one of substance delivery lumens 40, the flow of therapeutic substance to each of the other substance delivery lumens 40 continues uninterrupted.

Referring again to FIGS. 2A and 2B, a deflector 60 is disposed along an inner wall 62 of delivery lumen 40. In one embodiment, deflector 60 has a distal section 70, a medial section 72 and a proximal section 74. In one embodiment, distal section 70 can be supported by delivery lumen 40 by bonding distal section 70 to overhang section 47 of delivery lumen 40. Medial section 72 of deflector 60 can be disposed on inner wall 62 of delivery lumen 40, such that as delivery lumen section 42 rotates relative to delivery section 44 to form bend region 50, deflector 60 is positioned over the outside of the curvature of bend region 50. Proximal section 74 exits out of delivery lumen 40 and adhered to an outside wall 78 of delivery lumen 40 using an adhesive, such as glue or the like. Although, a particular method for securing deflector 60 to delivery lumen 40 has been described, one of ordinary skill in the art may be able to secure deflector 60 to delivery lumen 40 in a different manner and remain within the scope of the invention.

Deflector 60 can be any device that will provide a shield to protect the wall of delivery lumen 40 while being small enough, such that deflector 60 does not impact the track of catheter assembly 10 in any significant manner. In one embodiment, deflector 60 can be a ribbon member 60. Ribbon member 60 can be made thin, flexible and resilient such that ribbon member 60 can move and bend as delivery lumen sections 42 and 44 bend and move relative to each other. Positioning ribbon member 60 on the outside of the curvature of bend region 50 allows ribbon member 60 to shield the delivery lumen wall from piercing and the like by needle 46 as needle 46 moves through bend region 50. Ribbon member 60 also provides a surface upon which needle 46 can be made to track through bend region 50.

Ribbon member 60 is sized to ensure that the ribbon member fits into and along inner wall 62 of delivery lumen 40 without occluding or interfering with the ability of needle 46 to translate through bend region 50. For example, ribbon member 60 can have a thickness of between about 0.0005" and about 0.003". The width of ribbon member 60 may be between about 0.005" and about 0.015". The length of ribbon member 60 may be between about 1 cm and about 10 cm. Ribbon member 60 can be made from any suitable material, which allows ribbon member 60 to function, such as stainless steel, platinum, aluminum and similar alloy materials with similar material properties. In one embodiment, ribbon member 60 can be made from super-elastic alloys, such as nickel titanium alloys, for example NiTi.

As previously mentioned, transluminal angioplasty is a technique which is frequently used to enlarge a blood vessel, such as a coronary artery that has become occluded by the build-up of plaque, or to prevent or treat arterial restenosis and to promote angiogenesis response in the ischemic heart. As illustrated in FIGS. 3A–3C, in one embodiment, catheter assembly 10 can be used to reopen the narrowed lumen of coronary artery C. In a typical procedure, guidewire 18 can be introduced into the arterial system of the patient until the distal end of guidewire 18 reaches the narrowed lumen of artery C. Catheter assembly 10 is mounted on the proximal end of guidewire 18 and translated down guidewire 18 until catheter assembly 10 is positioned as desired in the narrowed lumen.

As shown in FIG. 3A, balloon 20 is in its deflated state, and needle 46 is disposed in its first retracted position, such that the needle's tissue-piercing tip 52 is located just inside of the surface of catheter body 12. For example, needle 46 can be pre-loaded into delivery lumen 40 until needle tip 52 is about one-half to a few centimeters proximal to the opening or needle exit notch 41. In this manner, catheter assembly 10 can track through coronary artery C without damaging the surrounding tissue or impeding the movement of catheter assembly 10. In the deflated state of balloon 20, needle 46 of delivery assembly 38 is in a first or rested position with needle 46 being generally parallel to longitudinal axis x of balloon 20. In this configuration, deflector 60 is also disposed in delivery lumen 40 substantially linear and parallel to axis x.

As illustrated in FIG. 3A, catheter assembly 10, having balloon 20 and delivery assembly 38, is advanced along guidewire 18 to a desired position in a physiological lumen, so that balloon 20 overlays at least a portion of a stenotic lesion. As shown in FIG. 3B, once catheter assembly 10 has been positioned within the reduced diameter lumen of diseased coronary artery C, balloon 20 is dilated by delivering a liquid to balloon 20 through inflation lumen 22. Inflating balloon 20 causes balloon 20 to engage and compact the material or tissue P built up on the internal wall of artery C. The inflation of balloon 20 also causes needle exit notch 41 to move proximate to or contact the physiological lumen wall. Needle 46 can then be pushed distally to pierce the physiological lumen wall for a fixed distance, which is determined, for example, with adjustment knob 57 (FIG. 1A) or by mechanical stop 80 (FIG. 4A). It will be appreciated that needle 46 must be able to track around bend region 50 so as to travel through delivery lumen 40 to extend beyond exit notch 41. As illustrated in FIG. 3B, deflector 60 is installed and supported inside of delivery lumen 40, such that as balloon 20 is inflated deflector 60 is positioned across bend region 50 on the outside of the bend curvature. As needle 46 is distally urged through bend region 50, deflector 60 helps to "bounce" the needle tip 52 off the delivery lumen wall, allowing needle 46 to travel through without digging into the delivery lumen wall (FIG. 3C).

After the predetermined volume of therapeutic agent has been injected through dispensing port 53 into the physiological lumen wall, needle 46 can be retracted into delivery lumen 40. Balloon 20 is then deflated and catheter assembly 10 is withdrawn from the physiological lumen for track to another treatment location.

It should be understood that although the invention has been described for use during or after an angioplasty procedure, catheter assembly 10, with delivery assembly 38, can be used to administer the therapeutic substance independent of any other procedure.

During some procedures it may be necessary or desirable to administer more than one type of therapeutic and/or diagnostic substance to the same tissue, or to administer the same therapeutic and/or diagnostic agent to more than one location in the tissue. Accordingly, a catheter assembly may be provided which includes a plurality of delivery assemblies 38 including more than one delivery lumen 40 and more than one needle 46. For example, a catheter assembly can include two needles which are positioned within two different delivery lumens spaced either radially and/or circumferentially from each other, for example, between 45° and 180° apart.

Beneficially, catheter assembly 10 has many applications. For example, by using adjustment knob 57 (FIG. 1A) to adjust the puncture depth of needle 46, the therapeutic substance can be administered to either the tissue of the artery wall or myocardial tissue. In applications involving the myocardium, catheter shaft 22 can be made torqueable to steer delivery lumen 40 toward the myocardium and properly position needle 46. Guidewire 18 can be made torqueable by any suitable means know by one of ordinary skill in the art.

The therapeutic substances and/or agents which can be delivered through needle 46 during a procedure can include, but are not limited to, antineoplastic, antiinflammatory, antiplatelet, anticoagulant, antifibrin, antithrombin, antimitotic, antiproliferative, antibiotic, antioxidant, antiallergic substances, and combinations thereof. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, mutamycin and actinomycin D. Examples of suitable cytostatic or antiproliferative agents include angiopeptin (a somatostatin analogue from Ibsen), angiotensin converting enzyme inhibitors such as Captopril® (available from Squibb), Cilazapril® (available from Hofman-LaRoche), or Lisinopril® (available from Merck); calcium channel blockers (such as Nifedipine), colchicine, fibroblast growth factor (FGF) antagonists, fish oil (omega 3-fatty acid), histamine antagonist, Lovastatin® (an inhibitor of HMG-CoA reductase, a cholesterol lowering drug from Merck), monoclonal antibodies (such as Platelet-derived Growth Factor (PDGF) receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. An example of an antiallergic agent includes Permirolast potassium. Other therapeutic substances or agents which may be appropriate include alpha-interferon, genetically engineered epithelial cells, dexamethasone, and growth factors such as FGF, PDGF, and Vascular Endothelial Growth Factor (VEGF). While the foregoing therapeutic substances or agents are well known for their preventative and treatment properties, the substances or agents are provided by way of example and are not meant to be limiting. Other therapeutic substances which are currently available or that may be developed are equally applicable for use with the present invention. The treatment of patients using the above-mentioned medicines is well known to those of ordinary skill in the art.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the scope of this invention.

What is claimed is:

1. A substance delivery apparatus, comprising:
   a hollow sheath defining an opening at a first end;
   a needle for administering a substance to a physiological lumen, said needle being movably disposed in said hollow sheath; and
   a mechanism for allowing said needle to translate from a first position where said needle is retracted within said hollow sheath to a second position where said needle extends a distance out from said opening, wherein said mechanism includes a balloon to position said opening to a predetermined position relative to said balloon,
   wherein said mechanism comprises a stainless steel ribbon, said ribbon operably supported by said hollow sheath.

2. The substance delivery apparatus of claim 1, wherein said hollow sheath defines a first section and a second section, wherein said first section is capable of moving relative to said second section.

3. A substance delivery apparatus, comprising:
   a hollow sheath defining an opening at a first end;
   a needle for administering a substance to a physiological lumen, said needle being movably disposed in said hollow sheath wherein said hollow sheath defines a first section and a second section, wherein said first section is capable of moving relative to said second section; and
   a mechanism for allowing said needle to translate from a first position where said needle is retracted within said hollow sheath to a second position where said needle extends a distance out from said opening, wherein said mechanism comprises a ribbon member which is configured to extend across a bend formed on said hollow sheath by said movement of said first section and said second section, said ribbon member providing a shield upon which a tip of said needle can bounce to translate over said bend.

4. A substance delivery apparatus, comprising:
   a hollow sheath defining an opening at a first end;
   a needle for administering a substance to a physiological lumen, said needle being movably disposed in said hollow sheath;
   a mechanism for allowing said needle to translate from a first position where said needle is retracted within said hollow sheath to a second position where said needle extends a distance out from said opening;
   a catheter assembly; and
   a balloon disposed at a distal end of said catheter assembly,
   wherein a first section of said hollow sheath rotates with respect to a second section of said hollow sheath in response to inflation of said balloon.

5. A device for delivering a substance to a desired area of treatment, comprising:
   a catheter body having a distal end and a proximal end;
   a balloon disposed at said distal end of said catheter body, said balloon being capable of inflating from a collapsed configuration to an expanded configuration;
   a first therapeutic substance delivery assembly including a first needle and a first delivery lumen, said first delivery lumen in fluid communication with said first needle to deliver a first therapeutic substance into a tissue of a physiological lumen, said first delivery lumen defining a first section and a second section, said first section being capable of moving relative to said second section in response to said inflating of said balloon; and
   a first deflector operably supported by said first delivery lumen.

6. The device of claim 5, wherein said movement of said first section relative to said second section forms a bend region in said first delivery lumen; said first deflector being disposed in said bend region to deflect said first needle through said bend region.

7. The device of claim 5, wherein said first deflector comprises a shaping ribbon made from a material taken from the group consisting of stainless steel, aluminum, platinum and NiTi.

8. The device of claim 5, further comprising a second therapeutic substance delivery assembly including a second needle and a second delivery lumen, said second delivery lumen in fluid communication with said second needle to deliver a second therapeutic substance into a tissue of a physiological lumen, said second delivery lumen defining a third section and a fourth section, said third section being capable of moving relative to said fourth section in response to said inflating of said balloon; and a second deflector operably supported by said second delivery lumen.

9. The device of claim 8, wherein said movement of said third section relative to said fourth section forms a bend region in said second delivery lumen; said second deflector being disposed in said bend region to deflect said second needle through said bend region.

10. The device of claim 5, further comprising a mechanical stop disposed in said first delivery lumen to limit the movement of said first needle.

11. A method for administering a therapeutic substance, comprising:

providing a catheter assembly including a first needle disposed in a first delivery lumen, said first delivery lumen defining a first exit notch;

positioning said first exit notch at a desired area of treatment within a physiological lumen; and deflecting said first needle with a first deflector as said first needle moves between a first position where said first needle is within said first delivery lumen to a second position where a portion of said first needle extends out from said first exit notch, wherein said catheter assembly comprises an inflatable balloon, wherein said second position comprises inflating said balloon from a collapsed configuration to an expanded configuration to cause said first exit notch to be proximate to a portion of said physiological lumen.

12. The method of claim 11, further comprising supplying a first therapeutic substance through said first needle to administer said first therapeutic substance to said desired area of treatment.

13. A method for administering a therapeutic substance, comprising:

providing a catheter assembly including a first needle disposed in first delivery lumen, said first delivery lumen defining a first exit notch;

positioning said first exit notch at a desired area of treatment within a physiological lumen;

deflecting said first needle with a first deflector as said first needle moves between a first position where said first needle is within said first delivery lumen to a second position where a portion of said first needle extends out from said first exit notch; and supplying a first therapeutic substance through said first needle to administer said first therapeutic substance to said desired area of treatment, wherein said catheter assembly comprises a balloon made from a porous membrane, said method further comprising supplying a second therapeutic substance into said balloon to inflate said balloon from a collapsed configuration to an expanded configuration and to discharge said second therapeutic substance out from said porous membrane.

14. A method for administering a therapeutic substance, comprising:

providing a catheter assembly including a first needle disposed in first delivery lumen, said first delivery lumen defining a first exit notch;

positioning said first exit notch at a desired area of treatment within a physiological lumen; and deflecting said first needle with a first deflector as said first needle moves between a first position where said first needle is within said first delivery lumen to a second position where a portion of said first needle extends out from said first exit notch, wherein said first delivery lumen comprise a first section and a second section, wherein said positioning comprises pivotally rotating said first section relative to said second section to contact a portion of said physiological lumen with said first exit notch.

15. The method of claim 14, wherein said pivotally rotating first section and second section form a bend region, said first deflector being disposed in said bend region to conform to a shape of said bend region.

16. The method of claim 15, wherein said first deflector comprises a shaping ribbon operably supported by said first delivery lumen, said shaping ribbon comprising a material taken form the group consisting of stainless steel, aluminum, platinum and NiTi.

17. A method for administering a therapeutic substance, comprising:

providing a catheter assembly including a first needle disposed in first delivery lumen, said first delivery lumen defining a first exit notch;

positioning said first exit notch at a desired area of treatment within a physiological lumen; and deflecting said first needle with a first deflector as said first needle moves between a first position where said first needle is within said first delivery lumen to a second position where a portion of said first needle extends out from said first exit notch, wherein said catheter assembly further comprises a second needle disposed in a second delivery lumen, said second delivery lumen defining a second exit notch; wherein said method further comprises:

position said second exit notch at said desired area of treatment within said physiological lumen; and deflecting said second needle with a second deflector as said second needle moves between a first position where said second needle is within said second delivery lumen to a second position where a portion of said second needle extends out from said second exit notch.

18. A method for administering a therapeutic substance, comprising:

providing a catheter assembly including a first needle disposed in first delivery lumen, said first delivery lumen defining a first exit notch;

positioning said first exit notch at a desired area of treatment within a physiological lumen; and deflecting said first needle with a first deflector as said first needle moves between a first position where said first needle is within said first delivery lumen to a second position where a portion of said first needle extends out from said first exit notch, wherein said catheter assembly further comprises a second needle disposed in a second delivery lumen, said second delivery lumen defining a second exit notch; wherein said method further comprises:

position said second exit notch at said desired area of treatment within said physiological lumen; and deflecting said second needle with a second deflector as said second needle moves between a first position where said second needle is within said second delivery lumen to a second position where a portion of said second needle extends out from said second exit notch, wherein said second delivery lumen comprises a third section and a fourth section, wherein said positioning comprises pivotally rotating said third section relative to said fourth section to contact a portion of said physiological lumen with said second exit notch, wherein said pivotally rotating third section and fourth section form a second bend region, said second deflector disposed in said bend region to conform to a shape of said second bend region.

19. A substance delivery apparatus, comprising:

a first hollow sheath defining a first opening;

a second hollow sheath defining a second opening;

a catheter body supporting said first hollow sheath and said second hollow sheath;

a first needle for administering a first substance to a physiological lumen, said first needle being movably disposed in said first hollow sheath;

a second needle for administering a second substance to said physiological lumen, said second needle being movably disposed in said second hollow sheath; and wherein said first needle extends and retracts within said first hollow sheath from a first position to a second position and said first needle extends a first distance out from said first opening, and wherein said second needle extends and retracts within said hollow sheath from a third position to a fourth position and said second needle extends a second distance out from said second opening, and wherein said first opening and said second opening are being separated by a predetermined angle, and wherein each of said first hollow sheath and second hollow sheath comprises a deflector disposed along an inner wall of each of said first hollow sheath and second hollow sheath.

20. The substance delivery apparatus of claim 19, wherein said predetermined angle is substantially between 45°–180°.

21. The substance delivery apparatus of claim 19, wherein first substance and second substance are the same substance.

22. The substance delivery apparatus of claim 19, further comprising:

an inflatable balloon coupled to an inflation lumen, said balloon being coupled to said catheter body;

a guidewire lumen coupled to said catheter body, and wherein inflating said inflatable balloon from a collapsed configuration to an expanded configuration position said first opening and said second opening proximate to two portions of said physiological lumen which are separated substantially by said predetermined angle.

23. A substance delivery apparatus, comprising:

a catheter assembly including a first needle disposed in a first delivery lumen, said first delivery lumen defining a first exit notch, said first exit notch positioned at a desired area of treatment within a physiological lumen;

a first deflector coupled to said catheter assembly to deflect said first needle as said first needle moves between a first position where said first needle is within said first delivery lumen to a second position where a portion of said first needle extends out from said first exit notch; and an inflatable balloon coupled to said catheter assembly, wherein inflating said inflatable balloon from a collapsed configuration to an expanded configuration positions said first needle to said second position to cause said first exit notch to be proximate to a portion of said physiological lumen.

24. The substance delivery apparatus of claim 23, wherein said catheter assembly further includes a second needle disposed in a second delivery lumen, said second delivery lumen defining a second exit notch; said second exit notch positioned at said desired area of treatment within said physiological lumen, and a second deflector to deflect said second needle as said second needle moves between a third position where said second needle is within said second delivery lumen to a fourth position where a portion of said second needle extends out from said second exit notch.

25. A substance delivery apparatus, comprising:

a hollow sheath defining an opening at a first end;

a needle for administering a substance to a physiological lumen, said needle being movably disposed in said hollow sheath; and a mechanism for allowing said needle to translate from a first position where said needle is retracted within said hollow sheath to a second position where said needle extends a distance out from said opening, wherein said needle being extended at an angle to the longitudinal direction of said hollow sheath, and wherein said hollow sheath comprises a deflector disposed along an inner wall of said hollow sheath.

* * * * *